(12) United States Patent
Shih

(10) Patent No.: US 8,486,009 B2
(45) Date of Patent: Jul. 16, 2013

(54) SYSTEMS AND METHODS FOR STEERING CATHETERS

(76) Inventor: Hue-Teh Shih, Houston, TX (US)

( * ) Notice: Subject to any disclaimer, the term of this patent is extended or adjusted under 35 U.S.C. 154(b) by 10 days.

(21) Appl. No.: 13/164,187

(22) Filed: Jun. 20, 2011

(65) Prior Publication Data

US 2012/0323174 A1 Dec. 20, 2012

(51) Int. Cl.
*A61M 31/00* (2006.01)

(52) U.S. Cl.
USPC ........................................ 604/95.04

(58) Field of Classification Search
USPC .................. 604/95.04, 95.05, 500, 508, 510, 604/523, 525, 528, 530; 606/108
See application file for complete search history.

(56) References Cited

U.S. PATENT DOCUMENTS

| | | | |
|---|---|---|---|
| 4,753,223 A * | 6/1988 | Bremer | 600/140 |
| 2010/0022876 A1 * | 1/2010 | Shih | 600/439 |

* cited by examiner

*Primary Examiner* — Nicholas Lucchesi
*Assistant Examiner* — Niyati D Shah
(74) *Attorney, Agent, or Firm* — Law Offices of Mark L. Berrier

(57) ABSTRACT

Systems and methods for steering catheters to facilitate advancing the catheters through the body, wherein the catheters employ multiple steering stages, each of which can move in multiple planes. The steering stages are independently controlled to enable them to form complex shapes. In one embodiment, the steerable catheter includes an elongated catheter body with the steering stages incorporated into the distal end of the catheter. The steering stages may incorporate multiple memory wires and corresponding heating elements that control the temperatures of the memory wires and consequently control the shapes of the wires and the steering stages in which they are embedded. The catheter may be any type of catheter (e.g., a lumen catheter) and may include features that enable the catheter to perform functions such as delivering therapies (e.g., ablation) to target tissues within the body.

9 Claims, 3 Drawing Sheets

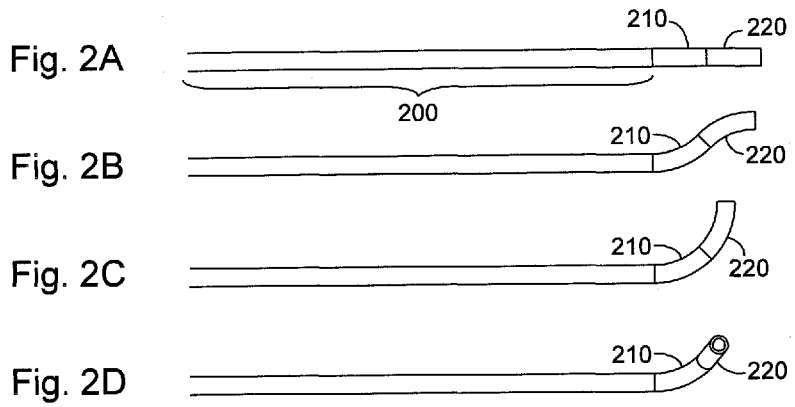
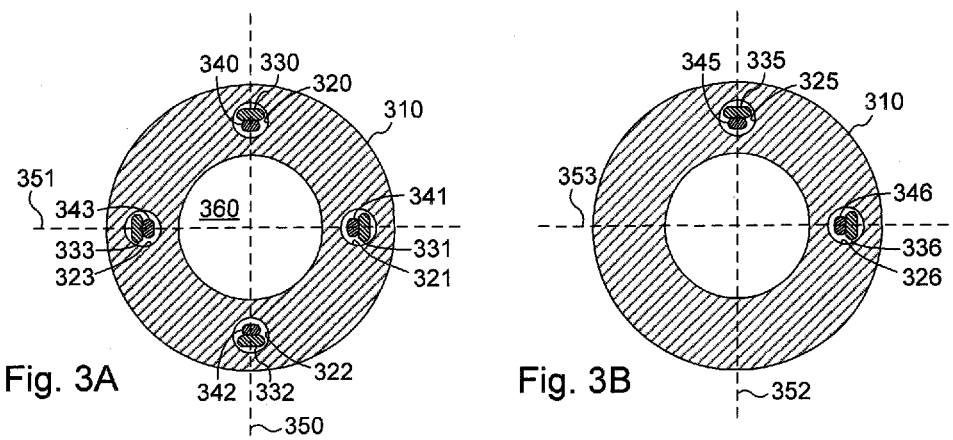
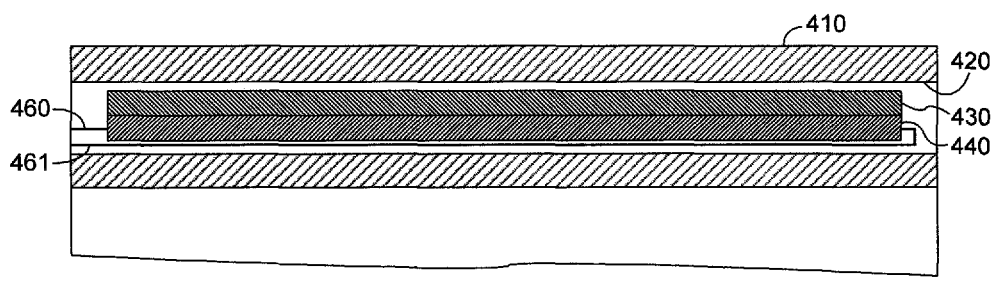

SYSTEMS AND METHODS FOR STEERING CATHETERS

BACKGROUND

1. Field of the Invention

The invention relates generally to medical devices and methods for their use. More particularly, the invention relates to systems and methods for steering catheters such as may be used to ablate tissues or to deliver materials within the body.

2. Related Art

In the medical field, catheters are used to deliver various therapies to locations within the body. For example, ablation catheters deliver therapy for the treatment of various diseases, such as skin spots, snoring, tumors, hemorrhage, arrhythmia and atherosclerosis. The catheters may employ a number of modalities to ablate tissue, including direct current (DC), radio frequency (RF), microwave, laser, ultrasound, chemical, cryogenic and rotary blade.

In a percutaneous procedure, one or more catheters are maneuvered into position within the body. In a typical cardiac ablation procedure, several catheters are advanced through the venous or arterial systems and positioned inside the heart. These are used to assess the etiology of the disease and then to treat it. The procedure may be iterative and make use of multiple sheaths and catheters in multiple steps. For example, in a conventional cardiac arrhythmia ablation procedure, catheters may first be maneuvered into various positions to denote the location and measure the timing of cardiac activation. This may be followed by the placement of an ablation catheter at a location with respect to the cardiac tissue where electrical activity is to be disrupted. The ablation catheter is used to burn or freeze the engaged tissue, altering the tissue behavior. Additional measurements may then be made to reassess the cardiac function. This process is repeated, alternating measurement and ablation, until the cardiac activation and resulting heart rhythm are modified as desired.

Multiple factors affect the success of such procedures. For example, one factor affecting the success of an ablation procedure is the reliability and stability of positioning (or repositioning) catheters. In an ablation procedure, the positioning not only affects the ability to take consistent measurements with a recording electrode, but also affects the ability to reliably ablate the intended target tissue. Mispositioning of the ablating element/electrode can result in failure to return to an ablation site to complete a lesion formation (an ablation), or can result in gaps in a line of lesions. These factors can make it difficult to apply the therapy, render the therapy ineffective, or even enhance the disease (e.g., make the cardiac tissue proarrhythmic).

It would therefore be desirable to provide systems and methods for facilitating positioning of catheters within the body which are more reliable, stable, and effective than prior systems and methods.

SUMMARY OF THE INVENTION

One or more of the problems outlined above may be solved by the various embodiments of the invention. Broadly speaking, the invention includes systems and methods for steering catheters within the body so that the catheters can be more easily and reliably positioned, and the stability of the positions better maintained.

One embodiment comprises a system for steering catheters such as may be used to ablate tissues or materials within the body using multiple independently controlled steering stages. In this embodiment, the steerable catheter includes an elongated catheter body and multiple steering stages. The steering stages are incorporated into a distal end of the catheter which is to be inserted into a body. Each of the steering stages is independently controlled, and can bend in multiple different planes to enable the catheter to assume different shapes, thereby facilitating selection of a desired path for the catheter through the body. The steering stages may incorporate multiple memory wires made of a metal such as nitinol, and corresponding heating elements. A control system may pass electrical current through the heating elements to control the temperatures of the memory wires and thereby control whether the memory wires relax and are allowed to bend or straighten, or assume a memorized shape. The catheter may be any type of catheter (e.g., a lumen catheter) and may include features that enable the catheter to perform functions such as delivering therapies (e.g., ablation) to target tissues within the body.

In the case of a conventional steerable catheter, mechanical pull wire(s) are fixed at the tip, run through the whole length of the catheter body, and are controlled by a steering mechanism at the proximal end of the catheter. The steerability of the catheter tip is affected by the deformation of the pull wire(s) at the more proximal portion of the catheter. When the catheter is deployed through a tortuous path, the pull wire(s) may be rotated and stretched proximally to the extent that no further mechanical force can be transmitted to the distal end. As a result, the catheter tip may not be able to assume the desired shape, and may not be able to steer the catheter in the desired direction.

An alternative embodiment comprises a method for facilitating insertion of a catheter into a body. The method includes providing a steerable catheter, introducing the catheter into the body, and advancing the catheter into the body while controlling each of the steering stages. This allows the catheter to be steered through a selected path through the body. The steerable catheter has multiple steering stages at its distal end, each being steerable in at least two different planes independently of the other steering stages. The steering stages of the catheter may be controlled by controlling heating elements and corresponding memory wires within the steering stages, thereby causing the steering stages to bend. Each of the steering stages may be controlled to bend in at least two different planes. Because the steering stages are independently controlled, they can each bend in different planes to form complex shapes at the end of the catheter. The steering mechanism and movement is independent of the proximal body of the catheter. Therefore, complex shapes and multiple directions can be achieved without being limited by the tortuous path that the proximal catheter body has to negotiate. After the steerable catheter has been advanced through the selected path, a therapy (e.g., ablation) can be delivered to target tissue using either the steerable catheter itself, or an additional catheter which is advanced through the path selected by the steerable catheter.

Numerous additional embodiments are also possible.

BRIEF DESCRIPTION OF THE DRAWINGS

Other objects and advantages of the invention may become apparent upon reading the following detailed description and upon reference to the accompanying drawings.

FIGS. 2A-2D are diagrams illustrating a catheter that employs a two-stage (or two-tier), two-plane-of-motion steering mechanism in accordance with one embodiment.

FIGS. 3A-3B are cross-sectional diagrams illustrating exemplary structures for steering stages in a catheter in accordance with one embodiment.

FIG. 4 is a diagram illustrating the structure of a catheter stage wall in accordance with one embodiment.

Figure 1:
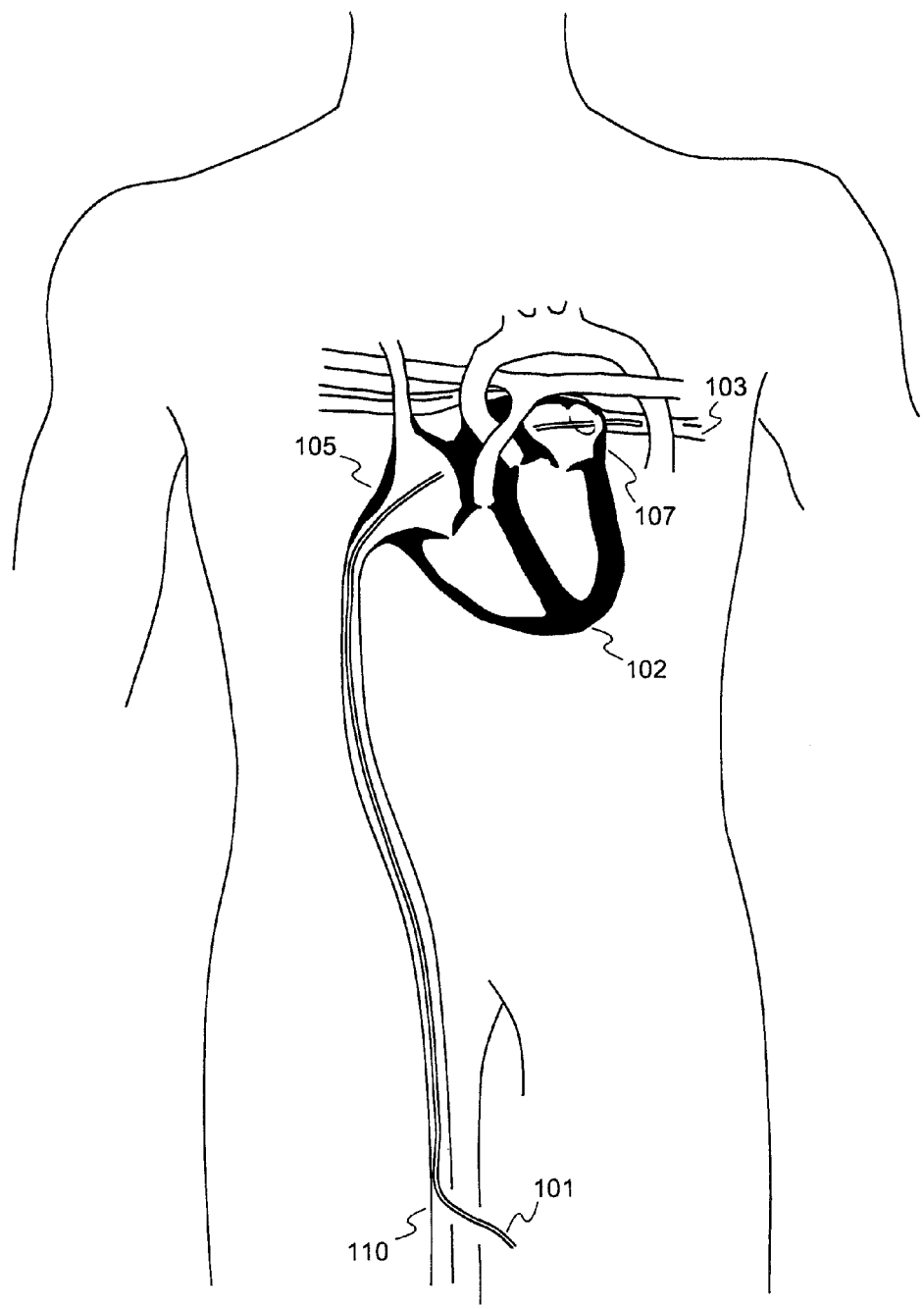
FIG. 1 is a diagram illustrating catheter placement within a body for an exemplary (e.g., cardiac ablation) procedure in accordance with the prior art.

While the invention is subject to various modifications and alternative forms, specific embodiments thereof are shown by way of example in the drawings and the accompanying detailed description. It should be understood that the drawings and detailed description are not intended to limit the invention to the particular embodiments which are described. This disclosure is instead intended to cover all modifications, equivalents and alternatives falling within the scope of the present invention as defined by the appended claims.

DETAILED DESCRIPTION OF EXEMPLARY EMBODIMENTS

One or more of the problems outlined above may be solved by the various embodiments of the invention. It should be noted that the embodiments described below are exemplary and are intended to be illustrative of the invention rather than limiting.

Broadly speaking, the invention includes systems and methods for steering catheters within the body so that the catheters can be more easily and reliably positioned, and the stability of the position better maintained.

One embodiment comprises a steerable catheter which includes multiple independently controlled steering stages at its distal end. Each steering stage has multiple memory wires embedded in its outer wall. The temperature of each memory wire is controlled to selectively cause the wire to either relax or return to a memorized shape, such as a curve or bend. When the memory wire returns to its memorized shape, it causes the steering stage in which it is embedded to bend in the same manner, thereby steering the catheter.

The proximal end of the catheter is connected to a control system. The control system regulates the temperatures of heating elements that are positioned next to the memory wires. When a heating element exceeds a transformation temperature of the adjacent memory wire, the wire assumes its memorized shape and bends the steering stage. When the heating element is below the transformation temperature, the memory wire can be deformed, so the steering stage can bend (or straighten) away from the memorized shape of the wire. The catheter may include various features in addition to the steering stages.

Before describing the invention in detail, it will be helpful to understand how certain terms are used in the present disclosure.

"Tissue," as used herein, refers to any material in the body. For example, tissue which is the target of ablation includes biological tissue or other targeted material, such as plaque.

"Catheter" refers to a rod- or tube-like device inserted into the body. Many catheters, such as those used in cardiac ablations, are very narrow (similar to a wire) so that they can be inserted through the skin and into a blood vessel. This allows the catheters to provide access to, or to deliver some distal end—effector (therapy), to some site in the body. Catheters may have many different configurations (e.g., lumen, non-lumen, etc.) and many different functions (e.g., positioning, recording, ablation, etc.)

"Distal" refers to a point or end of an object which is opposite a reference point on the object. In regard to a catheter, the reference point is typically the end of the catheter external to the body, so the distal end of the catheter is the end which is inserted into the body.

"Proximal" refers to a point or end of an object which is nearest the reference point on the object. In reference to a catheter, the proximal end of the catheter is the end which is external to the body and is typically in the hands of the clinician.

A "lumen" is a passage or duct. A lumen in a catheter or sheath is a duct through the catheter. For the purposes of this disclosure, a "lumen catheter" or "luminal catheter" is a sheath-like catheter or hybrid catheter-sheath which has a lumen inside the catheter through which another catheter can be inserted into the body.

"Memory wire" is wire made of an alloy that "remembers" its original, typically cold-forged shape, and which returns to that shape after being deformed by applying heat (a memory metal). Memory wire may also exhibit a two-way shape memory effect in which the material remembers two different shapes—one at lower temperatures, and one at higher temperatures. Memory metals may also be alternately referred to as a shape memory alloy, smart metal, memory alloy, muscle wire or smart alloy. One commonly used memory metal is nickel titanium, also known as nitinol. In this alloy, nickel and titanium are present in roughly equal amounts. The composition of the alloy can be adjusted to manipulate the transformation temperature, above which the memory metal recovers its memorized shape. Nitinol has been found to have a great degree of physiological and chemical compatibility with the human body.

Percutaneous transluminal catheter ablation is a minimally invasive therapy in which a series of catheters are inserted through the skin and advanced through the venous or arterial systems and positioned inside the heart or other tissues to either assess the etiology of or to treat the disease. Typically, a catheter or series of catheters are used to record the electrical signals from the location of interest and measure timing of cardiac activation followed by placement of an ablation catheter. The ablation catheter is then used to burn (or freeze) the engaged tissue, altering the tissue behavior. This process is performed iteratively, thereby modifying the heart rhythm. Percutaneous translumenal catheter ablation has been shown to be relatively safe and effective, for example, in treating selected heart rhythm disorders.

Ablation procedures typically employ a combination of devices appropriate to the task. Many of the devices are not directly involved in the ablation of the target tissue. These include, for instance, recording/measurement catheters that aid in determining performance of an organ/structure, determining the etiology of a disease, or in evaluating the efficacy of an ablation. Positioning/anchoring catheters/sheaths may also be used to guide placement of the ablation and recording/measurement catheters to the desired locations in the heart or other tissues. Any of these catheters/sheaths may be configured to implement steering stages as described herein.

FIG. 1 illustrates a conventional technique for positioning a catheter within a heart for the purpose of performing a procedure such as an ablation procedure. Access to the heart (102) is provided through the circulatory system itself, typically a femoral vein (110). Other vessels (e.g., 120) can also be used. A catheter or series of catheters (e.g., 101) are advanced through the vessels and into the heart. The catheters may, for example, be advanced into the right atrium (105), though the interatrial septum to the left atrium (107) and into pulmonary vein (103).

Typically, multiple catheters are placed simultaneously. On occasions, due to limited access and inability to simultaneously perform multiple functions with a single catheter, the same access site has to be shared by multiple catheters. In the case of an ablation procedure in which the ablation catheter cannot also record/measure data, the same access site has to be shared by the recording/measurement catheter and the ablation catheter. In this situation, a recording/measurement catheter is inserted, recordings/measurements are made, and then the recording/measurement catheter is withdrawn. An ablation catheter is then advanced into the heart and positioned at a predetermined site. The process is performed iteratively as necessary. A number of burns are then performed. It is not uncommon for ablation catheters to have to be removed and cleaned before being reintroduced to complete subsequent burn(s). Often, blood clots form on the electrodes of an RF catheter, making it ineffective. Also, catheters of differing configurations may have to be used.

Only one catheter is depicted in FIG. 1, but multiple catheters may be used simultaneously. For instance, a conventional pulmonary vein isolation procedure that uses multiple catheters simultaneously requires four components: a first positioning/anchoring sheath; a recording/measurement/positioning catheter which is inserted through the first sheath; a second sheath; and an ablation catheter which is inserted through the second positioning/anchoring sheath. While the simultaneous use of these catheters avoids the need to repeatedly withdraw and insert the catheters, the use of multiple catheters is much more invasive than the use of a single catheter at a time (or a single recording/ablation luminal catheter/sheath with a single recording/measurement/positioning/anchoring catheter inserted through the luminal catheter that functions both as a sheath and an ablation catheter).

In conventional cardiac ablation procedures, gaps can make the ablation ineffective and can possibly be arrhythmogenic (possibly creating a circuit around the lesion). A labyrinth-like arrangement of conductive tissue resulting from an ablation can effectively create a circuit with a delay which is sufficient to reinitiate a wave of activation after the refractory period of the local cells, but before it would be initiated by proper pacing. It is therefore important to be able to easily and efficiently advance the catheter through the blood vessels and properly position the catheter to ablate the target tissue.

FIGS. 2A-2D are diagrams illustrating a catheter that employs a two-stage (or two-tier), two-plane-of-motion steering mechanism to allow the catheter to more easily be steered through the body to the target tissue. Referring to FIG. 2A, the catheter has an elongated main body 200 and includes two steerable stages (210, 220) at its distal end. Main body 200 of the catheter (which may also be referred to as the proximal portion of the catheter) is rigid enough to allow that catheter to be pushed inward (toward the distal end), but is flexible enough to allow the body to follow the path in which it is steered by stages 210 and 220. Stages 210 and 220 are independently controlled so that they can be turned in various directions, independent of each other. Stages 210 and 220 are indicated as separate components for the purposes of showing the manner in which they can be steered. Typically, the stages will be integral to the catheter and will not necessarily be visibly distinguishable without flexing the stages.

FIG. 2A shows that catheter with both steerable stages in a straightened position. FIGS. 2B-2D shows the catheter with steering stages 210 and 220 in various exemplary positions. For instance, in FIG. 2B, stage 210 is curved upward, while stage 220 is curved downward, thereby forming an "S" shape. In FIG. 2C, both the stages 210 and 220 are curved upward to provide increased curvature in a single direction. In FIG. 2D, stage 210 is curved upward (toward the top of the page), while stage 220 is curved in an orthogonal plane (out of the page). These figures show just a few examples of the shapes that can be achieved by the stages to facilitate steering of the catheter through the body.

Referring to FIGS. 3A-3B, a pair of cross-sectional diagrams illustrating exemplary structures for the steering stages are shown. In both of these figures, the steering mechanism employs memory wire to conform the steering stage to a shape that allows the stage to steer the catheter. The structure of FIG. 3A uses embedded memory wires on four sides of the stage, while the structure of FIG. 3B uses embedded memory wires on two sides of the stage.

Referring to FIG. 3A, the steering stage has four cavities (320-323) within the outer catheter wall 310. Inside each cavity is a memory wire (330-333) and a heating wire (340-343). The illustrated embodiment is a lumen catheter. Lumen 360 is provided to allow another catheter to be inserted into the body through the lumen catheter. The lumen catheter itself can also be designed to provide various features aside from the ability to steer the catheter. For instance, the Lumen catheter may be configured as an ablation catheter (see U.S. Patent Application Pub. 2010/0022876, which is hereby incorporated by reference), in which case electrical conductors used for operation of the ablation tip may be incorporated into the steering stage (e.g., embedded in the stage wall).

In this embodiment, each memory wire is constructed from a two-way memory material, so that it takes on a first shape at a lower temperature and a second shape at a higher temperature. When electrical current is passed through one of the heating wires, it generates heat that raises the temperature of the adjacent memory wire. This causes the memory wire to assume the higher-temperature shape. When the current through the heating wire is reduced, the temperature of the heating wire and adjacent memory wire decreases. This causes the memory wire to move toward the lower-temperature shape.

In this embodiment, pairs of memory wires (and corresponding heating wires) are positioned on opposite sides of the catheter. Each pair lies within a different plane through the axis of the catheter. (In this context, "axis" is used to refer to a line through the center of the steering stage when it is straight.) A first pair of the memory wires (330, 332) lies on plane 350, while a second pair of the memory wires (331, 333) lies on plane 351. Plane 350 is orthogonal to plane 351. Each pair of memory wires is configured to move (e.g., curve) the stage within a corresponding one of the planes. For instance, memory wires 330 and 332 could curve the stage within plane 350, while memory wires 331 and 333 could curve the stage within plane 351. Alternatively, memory wires 330 and 332 could be configured to curve the stage within plane 351, while memory wires 331 and 333 could be configured to curve the stage within plane 350.

Referring to FIG. 4, a diagram illustrating the structure of a catheter stage wall in accordance with one embodiment is shown. FIG. 4 is a partial cross-section of the stage wall through one of the cavities. The outer wall 410 of the catheter has a cavity 420 therein. Memory wire 430, as well as heating element 440 are positioned within cavity 420. Memory wire 430 may be formed from one-way or two-way memory material. Heating element may be a simple resistive element (e.g., high-resistance wire) or any other suitable means for heating the memory wire. Conductive wires 460 and 461 connect heating element 440 to a control system external to the catheter. The control system controls the amount of current that is carried by wires 460 and 461 to heating element 440, and thereby controls the amount of heat generated by the heating element. Depending upon the temperatures at which memory wire 430 is activated to assume its memorized shape(s), it may be sufficient for control purposes to heat the memory wire and allow it to cool through dissipation of heat from the wire. In alternative embodiments, it may be possible to cool the memory wire by passing fluid through the catheter or using other means to reduce the temperature.

As noted above, the steering stage may use two-way memory wire to achieve the desired curvature of the stage. For instance, each of memory wires 330 and 332 can be designed to curve the stage upward by some number of degrees in plane 350 at higher temperatures and downward by some number of degrees in plane 350 at lower temperatures. In an alternative embodiment, memory wire having a one-way memory effect can be used instead of memory wire having a two-way memory effect. In such an embodiment, memory wire 330 could be designed to curve the stage upward by some number of degrees in plane 350 when activated to take on its memorized shape, and memory wire 332 could be designed to curve the stage upward by some number of degrees in plane 350 when it is activated. When one of the memory wires is activated to take on its memorized shape, the opposite memory wire is allowed to bend away from its memorized shape (which curves in the opposite direction).

The amount of steering (degrees by which each stage can turn) can vary in different embodiments. While some stages may be configured symmetrically so that they may turn by the same number of degrees in opposite directions (e.g., 30° to the left or to the right), other stages may be configured asymmetrically so that they can turn by some number of degrees in a first direction, or a different number of degrees in the opposite direction. The steerable stages need not be configured to conform to simple curves, but may instead be designed to take on more complex shapes, such as a bend or a helical shape.

By controlling the temperature of each of memory wires 330-333, the steering stage can be caused to curve in any direction. As explained above, memory wires 330 and 332 can bend the stage in plane 350 and memory wires 331 and 332 can bend the stage in plane 350. If one of these pairs of memory wires is activated while the other is relaxed, the stage will bend in the corresponding plane (350 or 351). Alternatively, both pairs can be activated to various degrees to bend the stage in a plane between planes 350 and 351. As noted above, each steering stage is independent of the other(s), so the combination of two or more stages may form simple curves in a single pane or more complex shapes in which the different stages bend in different planes. It should also be noted that the mechanism for controlling the steering stages is independent of and unaffected by the shape of the main body (proximal portion) of the catheter, allowing the catheter to be steered through more tortuous paths than conventional steerable catheters.

Referring to FIG. 3B, a diagram illustrating the structure of a steering stage in an alternative embodiment is shown. In this embodiment, rather than four memory wires, only two memory wires are embedded in the catheter wall. The configuration of each of the individual cavities (325, 326), memory wires (335, 336) and heating wires (345, 346) may be the same as the corresponding elements of FIG. 3A, but only one memory wire is used to change the shape of the stage within each of the planes (352, 353) through the stage. It is contemplated that memory wire 335 would move the stage within plane 352, while memory wire 336 would move the stage within plane 353 to prevent twisting of the catheter.

It should be noted that, although the present disclosure refers to the memory metal components of the steering stages as "wires", these components need not have a conventional, uniform, round cross-section, but may have any shape that is effective to cause bending of the steering stages. "Wire" should therefore be broadly construed to include any suitable shape of the memory element constructed of any suitable material embedded in the steering stages.

Figure 5A:
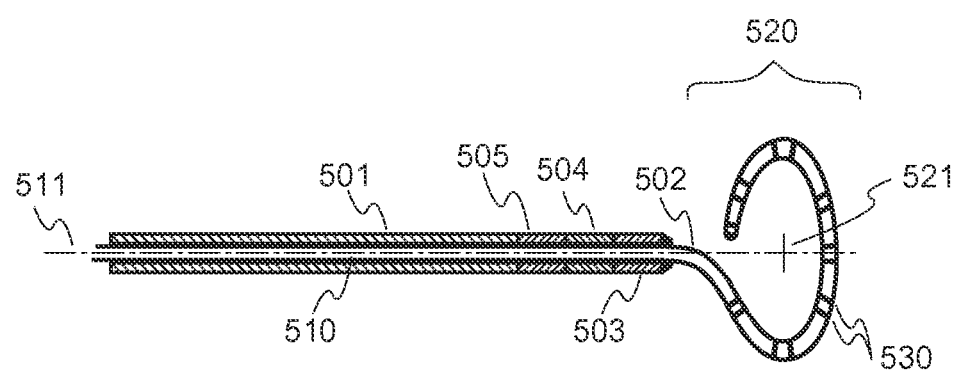
FIGS. 5A-5B are diagrams illustrating steerable lumen catheters that are used in conjunction with other catheters in accordance with alternative embodiments of the invention.
Figure 5B:
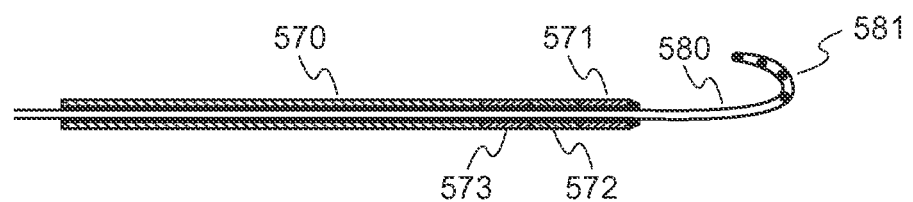

FIGS. 5A-5B are diagrams illustrating steerable lumen catheters that are used in conjunction with other catheters in accordance with alternative embodiments of the invention. FIG. 5A is an illustration of an exemplary system which comprises a steerable ablation luminal catheter 501 and a recording/positioning catheter 502. Both ablation catheter 501 and recording/positioning catheter 502 may also serve other purposes, such as recording catheters, anchoring catheters, etc. Ablation catheter 501 includes a non-contact ablation element 503 which is located at or close to the tip of the catheter. Steering stages 504 and 505 are located adjacent to non-contact ablation element 503, which in this embodiment is positioned at the tip of the ablation catheter. In an alternative embodiment, the steering stages could be located at the tip of the catheter, with the ablation element adjacent to the steering stages toward the proximal end of the catheter.

Non-contact ablation element 503 may, for example, be an ultrasound transducer which is configured to deliver energy in the form of ultrasonic waves to the tissue targeted for ablation. The ultrasound energy destroys the tissue by heating the tissue, creating lesions that can block unwanted electrical pathways. The ultrasound energy, however, can be delivered from a stand-off position. That is, the ablation element need not be in contact with the target tissue. The ultrasonic waves can travel through fluids between the ablation element and the tissue so that the target tissue, rather than the intervening fluid, is destroyed. As noted above, recording elements can be mounted at other locations on the luminal catheter in order to provide recordings and measurements that complement those of the recording/positioning catheter.

Ablation catheter 501 is itself a luminal catheter. Recording/positioning catheter 502 can therefore be inserted within the lumen of ablation catheter 501, much like using a sheath. Conventionally, a sheath in an ablation procedure serves no purpose other than to provide a conduit through which a functional (e.g., ablation or recording/measurement) catheter is inserted. By incorporating an ablation element and possibly several recording elements onto the luminal catheter/sheath (or alternatively incorporating a lumen into an ablation/recording catheter), twice as many functional instruments can be inserted into the body with no increase in the invasiveness of the procedure and no increase in the trauma to the affected tissue caused by the insertion procedures. This provides a substantial advantage over conventional techniques. With regard to procedures in which separate ablation and recording/measurement catheters are repeatedly inserted and withdrawn from the body, this embodiment reduces the amount of time required to perform the procedure and reduces the possibility of catheter positioning errors. With respect to procedures in which multiple catheters are simultaneously inserted into the body, this embodiment reduces the amount of space occupied by the surgical instruments because it reduces the number of catheters and sheaths, from typically four (two sheaths, an ablation catheter and a recording/measurement catheter) to two (a luminal catheter/sheath for ablation and recording that also serves as the conduit for a second recording/positioning/anchoring catheter), thereby reducing the trauma.

Recording/positioning catheter 502 has a main body 510 and a distal portion 520 which includes an array of electrodes (e.g., 530). The distal portion 520 can be formed into a loop. The loop is placed in contact with the tissue (e.g., the myocardium or blood vessel wall) and enables the accurate positioning and stable anchoring of ablation catheter 501 (or more specifically ablation element 503), which can be moved forward or backward over main body 510. In the embodiment of FIG. 5A, loop portion 520 is substantially concentric with and perpendicular to the axis of main body 510 of catheter 502. As a result, if loop center 521 is coaxial with a cavity in which the catheter is inserted, ablation element 503 remains substantially centered in the cavity, regardless of the movement of ablation catheter 501 over main body 510. Loop portion 520 can alternatively be configured so that the center of the loop is off-axis rather than being concentric with catheter 501.

Another alternative embodiment is shown in FIG. 5B. FIG. 5B shows an ablation system including a steerable ablation catheter 570 (with ablation element 571) and a recording/positioning/anchoring catheter 580 which is inserted through the lumen of the ablation catheter. In this embodiment, recording/positioning/anchoring catheter 580 does not have a loop at the distal end of the catheter, but instead has a hook-shaped portion. This hook-shaped portion serves essentially the same purpose as the loop portion of the other embodiments in that it is placed against some part of the tissue to stabilize the recording/positioning catheter and allow the ablation catheter to be positioned and anchored by sliding it over the recording/positioning/anchoring catheter.

The loop shape can be an integral (fixed) feature of the catheter or (re)configurable. The catheter may have a lumen and the distal portion of the catheter may be constructed of a flexible material that takes the shape of a wire that is introduced into the lumen. Alternatively, the shape may be manipulated (e.g., by employing memory wire in a manner similar to the steering stages).

Another purpose of the loop portions and hook portions of the recording/positioning/anchoring catheters is to enable recording and measurements of the tissue characteristics (e.g., electrical potentials). The recording/positioning/anchoring catheters therefore include electrodes (e.g., 530, 581) positioned on the loop and hook-shaped portions. The electrodes are coupled to recording/measurement/stimulation unit(s) at the proximal end of the catheter. The recording/measurement/stimulation units are configured to transmit stimulus signals to the electrodes if necessary and to receive signals from the electrodes via wiring through the catheter. When the recording/positioning/anchoring catheters are positioned with the respective loop/hook portions against the tissue, the electrodes can be used to record and measure the tissue characteristics. The electrodes may be in contact with the tissue, or they may not be in contact with the tissue, depending upon the circumstances. Because the recording/positioning/anchoring catheters and corresponding electrodes can remain in place during the ablation procedure, consistent before-and-after recordings and measurements can be made. The electrodes are used in the assessment/evaluation of the effectiveness of an ablation. The electrodes can be positioned to record electrical (cardiac) signals or to stimulate (pace) the heart.

It should be noted that additional electrodes can be positioned on the ablation luminal catheter/sheath. These electrodes may, for example, be placed on the body of the ablation catheter on the side of the ablation element opposite the distal end of the catheter. The electrodes of the recording/positioning/anchoring catheter and ablation catheter/sheath would therefore be on opposite sides of the lesion created by the ablation procedure. This allows the operator to assess the effect of the ablation, i.e. whether there is a disconnection or disruption of electrical conduction between the distal and the proximal portion of the tissue, without the need to replace the ablation ensemble with the recording ensemble for this purpose, thus shortening procedure time.

There may be numerous alternative embodiments of the system. For example, it is contemplated that the steering stages may be incorporated into many different types of catheters, and is not limited to ablation catheters or lumen catheters such as are described above. There are a number of suitable memory metals from which the memory wires can be formed, and the materials from which the catheter body and other components can be constructed are also quite varied. The steering stages can use mechanisms other than memory wire (e.g., pullable tendons within the catheter) to control the curvature of each stage. While the embodiments described above (specifically in connection with FIGS. 2A-2D) employ two steerable stages, alternative embodiments may use a greater number of these stages in order to guide the catheter through the body. The stages can be identically configured, or they may be configured in different ways.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein and recited within the following claims.

What is claimed is:

1. A steerable catheter comprising:
an elongated catheter body, wherein the catheter body has a proximal end and a distal end; and
a plurality of controlled steering stages at the distal end of the catheter body;
wherein each of the steering stages is steerable independently of the other steering stages;
wherein each of the steering stages is steerable in at least two different planes, wherein at least a first one of the steering stages is steerable in a first plane while at least a second one of the steering stages is being steered in either a first plane, or a second plane which is different from the first plane;
wherein each of the steering stages has an outer wall having a plurality of memory wires embedded therein, wherein the memory wires in each steering stage are not connected to the memory wires of other ones of the steering stages; and wherein each of the memory wires has a corresponding heating element positioned adjacent to and thermally coupled to the memory wire, and wherein a temperature of the heating element is controlled, thereby causing the adjacent memory wire to alternately relax or bend toward a memorized shape, thereby controlling bending of the steering stage, thereby steering the catheter;

a control system coupled to the proximal end of the steerable catheter, wherein the control system is coupled to each of the heating elements and regulates the temperatures of the heating elements, thereby controlling a temperature of each of the corresponding memory wires.

2. The steerable catheter of claim 1, wherein the memory wires comprise a nickel-titanium alloy.

3. The steerable catheter of claim 1, wherein each of said steering stage has at least two memory wires embedded therein, wherein each of the memory wires lies within a different plane through an axis at the center of the steering stage.

4. The steerable catheter of claim 1, wherein each of said steering stage has at least two separate pairs of said memory wires embedded therein, wherein each of said pair of the memory wires lies within a different plane through an axis at the center of the steering stage, and wherein the memory wires of each of said pair are embedded in opposite sides of the steering stage.

5. The steerable catheter of claim 1, wherein the steerable catheter comprises a lumen catheter.

6. The steerable catheter of claim 5, wherein the outer wall has a plurality of cavities therein, wherein each of the cavities has one of the plurality of memory wires and the corresponding heating element inserted therein, and wherein the each of the cavities is located between a lumen and exterior of the lumen catheter.

7. The steerable catheter of claim 1, wherein steerable catheter includes an ablation element at or adjacent to the distal end of the catheter.

8. The steerable catheter of claim 1, wherein each of said steering stage is steerable independent of a shape of a proximal portion of the steerable catheter.

9. The steerable catheter of claim 1, wherein the outer wall has a plurality of cavities therein, wherein each of the cavities has one of the plurality of memory wires and the corresponding heating element inserted therein.

* * * * *